(12) United States Patent
Kumar et al.

(10) Patent No.: US 10,512,507 B2
(45) Date of Patent: Dec. 24, 2019

(54) METHOD AND SYSTEM FOR AUTOMATIC ESTIMATION OF UTILITY OF ADAPTIVE RADIATION THERAPY RE-PLANNING

(71) Applicant: KONINKLIJKE PHILIPS N.V., Eindhoven (NL)

(72) Inventors: Prashant Kumar, Banggalore (IN); Yogisha Mallya, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 991 days.

(21) Appl. No.: 14/908,264

(22) PCT Filed: Jul. 16, 2014

(86) PCT No.: PCT/IB2014/063140
§ 371 (c)(1),
(2) Date: Jan. 28, 2016

(87) PCT Pub. No.: WO2015/019215
PCT Pub. Date: Feb. 12, 2015

(65) Prior Publication Data
US 2016/0175052 A1    Jun. 23, 2016

Related U.S. Application Data

(60) Provisional application No. 61/862,535, filed on Aug. 6, 2013.

(51) Int. Cl.
*A61B 34/10* (2016.01)
*A61N 5/10* (2006.01)
*A61N 7/00* (2006.01)
*A61B 18/00* (2006.01)

(52) U.S. Cl.
CPC ............ *A61B 34/10* (2016.02); *A61N 5/1037* (2013.01); *A61N 7/00* (2013.01); *A61B 2018/00577* (2013.01); *A61B 2034/107* (2016.02); *A61B 2576/00* (2013.01); *A61N 5/1038* (2013.01)

(58) Field of Classification Search
None
See application file for complete search history.

(56) References Cited

U.S. PATENT DOCUMENTS

| | | | |
|---|---|---|---|
| 7,574,251 B2 | 8/2009 | Lu et al. | |
| 7,756,359 B1 | 7/2010 | Nord et al. | |
| 8,222,616 B2 | 7/2012 | Lu et al. | |

(Continued)

FOREIGN PATENT DOCUMENTS

| | | | | |
|---|---|---|---|---|
| EP | 1 970 097 | * | 7/2006 | ............... A61N 5/10 |
| EP | 1970097 | | 9/2008 | |
| EP | 2574374 | | 4/2013 | |

(Continued)

*Primary Examiner* — Carolyn A Pehlke
*Assistant Examiner* — Marjan Saboktakin

(57) ABSTRACT

A method and system determines a utility of performing a re-planning on a patient during a radiation therapy planning. Quality improvements which may be made possible by re-planning the patient are automatically estimated, independent of clinician bias. This enables the clinician to make an informed decision regarding whether to re-plan the patient in a fast and efficient manner. This achieves more uniformity and predictability in the adaptive re-planning.

20 Claims, 2 Drawing Sheets

(56) References Cited

U.S. PATENT DOCUMENTS

Figure 1:
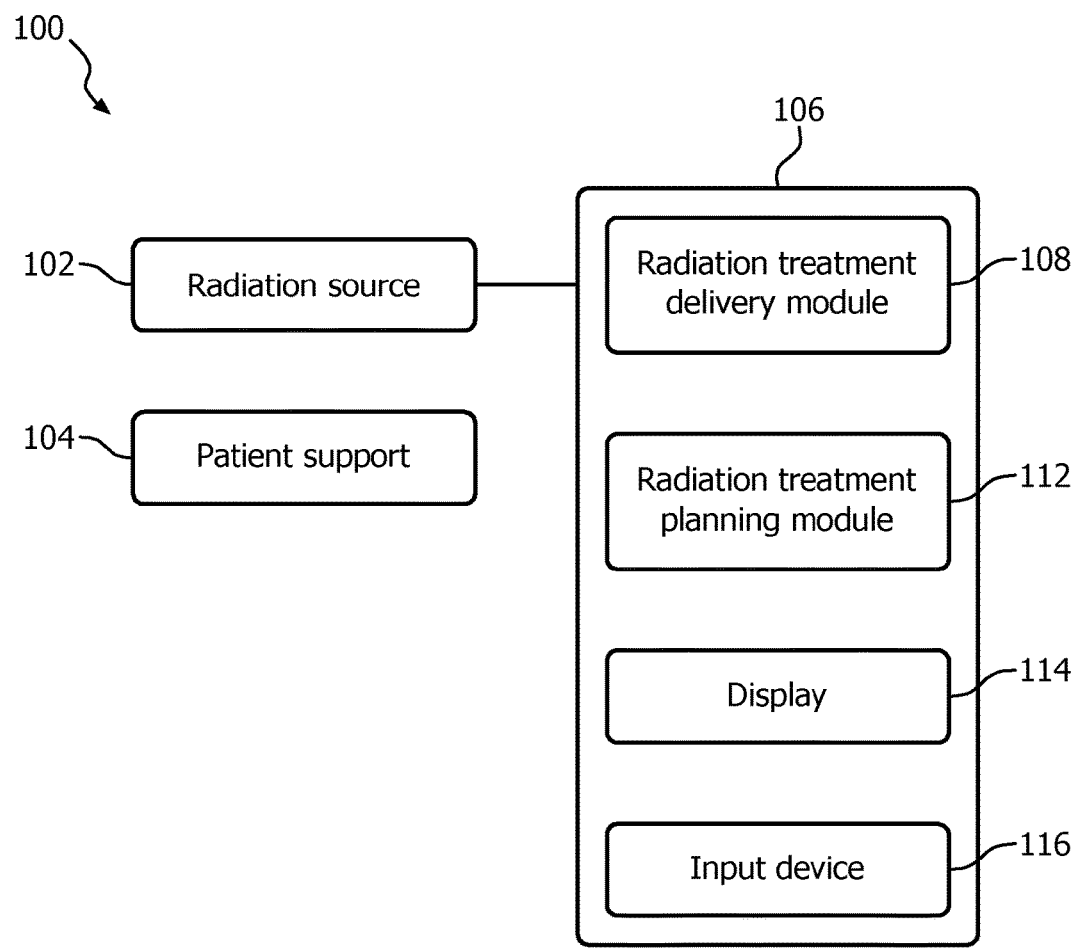

2004/0254448 A1  12/2004  Amies et al.
2006/0074292 A1   4/2006  Thomson et al.

FOREIGN PATENT DOCUMENTS

| WO |    2005/031629 |   | 4/2005 |              |
|----|----------------|---|--------|--------------|
| WO | WO 2005/031629 | * | 4/2005 | ...... G06F 19/00 |
| WO |    2007/002642 |   | 1/2007 |              |
| WO | WO 2007/002642 | * | 1/2007 | ...... A61B 5/05 |
| WO |    2008/013598 |   | 1/2008 |              |

* cited by examiner

METHOD AND SYSTEM FOR AUTOMATIC ESTIMATION OF UTILITY OF ADAPTIVE RADIATION THERAPY RE-PLANNING

CROSS REFERENCE TO RELATED APPLICATIONS

This application is the U.S. National Phase application under 35 U.S.C. § 371 of International Application No. PCT/IB2014/063140, filed Jul. 16, 2014, published as WO 2015/019215 on Feb. 12, 2015, which claims the benefit of U.S. Provisional Patent Application No. 61/862,535 filed Aug. 6, 2013. These applications are hereby incorporated by reference herein.

The present application relates generally to a method and system for radiation therapy planning. Radiation therapy is the process by which trained medical clinicians plan and execute a delivery of ionizing radiation to a patient. The goal(s) of radiation therapy can vary widely. Very commonly this therapy is used to treat a disease such as cancer by ionizing the diseased tissue, thereby destroying the diseased tissue. A central goal of radiation therapy planning is to control the radiation delivery to maximize radiation exposure to the targeted region(s) within the patient's body (i.e., diseased tissue), while minimizing radiation exposure to protected region(s) within the patient's body (i.e., healthy tissue).

As commonly implemented, radiation therapy begins with a detailed three-dimensional imaging scan of the patient's body, such as a computed tomography (CT) scan. The clinician or other medical professional specifies several characteristics of a radiation therapy plan based on the imaging data. For example, using the imaging data, the clinician can identify one or more specific targeted and protected regions within the patient's body. The clinician can further specify a minimum radiation dosage to be delivered to each targeted region (i.e., enough to destroy the diseased tissue), a maximum radiation dosage to be delivered to each protected region (i.e., to limit damage to healthy tissue), and several other desired characteristics of a radiation therapy. Once the plan is finalized, the radiation therapy is then administered to the patient.

Quite often, a clinically significant amount of time passes between the imaging data scan and the delivery of radiation treatment to the patient. More specifically, it takes some amount of time to process the data generated by the imaging scanner in order to produce useful images of the patient's body. More time is then needed for the clinician to review and analyze the imaging data in order to prepare an appropriate radiation delivery plan to implement the therapy. And finally, it takes yet further time to schedule the patient's visit to a medical facility in order to administer the radiation delivery. All in all, in most situations, at least a few days and perhaps even a few weeks or months pass between the imaging data scan of the patient and the radiation delivery to the patient. During that time period, the locations and orientations of the patient's internal organs may very well have changed. Such movement is caused, for example, by the patient's breathing, heart beating, weight gain or loss, digestive processes, and other physiological processes. In addition, the size and orientation of the targeted tumor or other targeted region may very well have grown, shrunk, or changed shape. The deformations resulting from these and other considerations can often be clinically significant, especially given the high accuracy of the imaging scanners and the radiation delivery equipment in use today.

Adaptive re-planning is a process by which a radiation therapy plan is re-assessed close in time prior to the actual radiation delivery. The process attempts to account for changes in patient anatomy which have occurred after the initial imaging scan was performed to generate the about-to-be-delivered radiation therapy plan. Adaptive re-planning presents potential benefits to the patient in terms of an improved radiation delivery, but at the same time the workload involved is increased. Radiation therapy planning is a tedious and time consuming task, especially if the resulting plan needs to be certified or otherwise accepted by the clinician so that it can be approved for actual delivery to the patient. The amount of time required for creating a new clinically acceptable radiation therapy plan from scratch with respect to the latest imaging data of the patient substantially increases the clinician's workload. So, in clinical practice one would prefer to use quantification approaches which could establish the utility of re-planning the patient without the clinician having to actually create a new radiation treatment plan, enabling the clinician to make an informed decision before starting the re-planning process.

Various indicators can be used to evaluate the utility of a re-planning, without the clinician actually generating a clinically acceptable radiation therapy plan. Such indicators include, for example, the amount of change or discrepancy which exists between the earlier and the later images of the patient; applying the radiation delivery plan generated from the earlier image to the later image of the patient, and analyzing the resulting dose statistics; and yet other indicators. These solutions are useful short cuts but given the complexity of radiation therapy planning the only certain way to know what can actually be achieved by re-planning is for a clinician to actually create a new clinically acceptable radiation therapy plan based on the latest image of the patient.

The present disclosure presents a framework for automatic estimation of quality improvements which may be possible by re-planning the patient, so that the clinician can make an informed decision regarding whether to re-plan the patient in a fast and efficient manner. Using the combination of deformable image registration and auto-planning of a radiation therapy, the framework automatically produces clinician-independent treatment plans and compares radiation dose statistics of the involved targeted and protected regions to decide a re-planning utility. The comparison data is generated independently from the clinician, automatically creating treatment plans based on the earlier and later images of the patient, and thus provides more uniformity and predictability in the adaptive re-planning process. In this way, the decision whether to clinically re-plan a patient can be guided by a quantified approach based on one or more information points.

A method and system for determining a utility of performing a re-planning on a patient during a radiation therapy planning is provided. A first imaging data set of the patient is registered with a second imaging data set of the patient to generate a transformation map, wherein the first imaging data set comprises at least one segmented region of interest, and the second imaging data set is recorded at a later time than the first imaging data set. The at least one segmented region of interest in the first imaging data set is propagated to the second imaging data set utilizing the transformation map, to generate a corresponding segmented region of interest in the second imaging data set. An automated inverse radiation therapy planning technique is applied to the first imaging data set based on one or more user-specified desired radiation delivery characteristics derived from the first imaging data set, to generate a first radiation delivery plan. The automated inverse radiation therapy planning technique is also applied to the second imaging data set based on one or more user-specified desired radiation delivery characteristics derived from the second imaging data set, to generate a second radiation delivery plan. The first radiation delivery plan is applied to the second imaging data set, to generate a first radiation dose grid identifying a radiation dosage received at each imaging element of the second imaging data set by the first radiation delivery plan. A second radiation dose grid is also generated, identifying a radiation dosage received at each imaging element of the second imaging data set by the second radiation delivery plan.

Radiation therapy planning systems incorporating the methods are also provided.

Numerous advantages and benefits will become apparent to those of ordinary skill in the art upon reading the following detailed description of several embodiments. The invention may take form in various components and arrangements of components, and in various process operations and arrangements of process operations. The drawings are only for the purpose of illustrating many embodiments and are not to be construed as limiting the invention.

Figure 2:
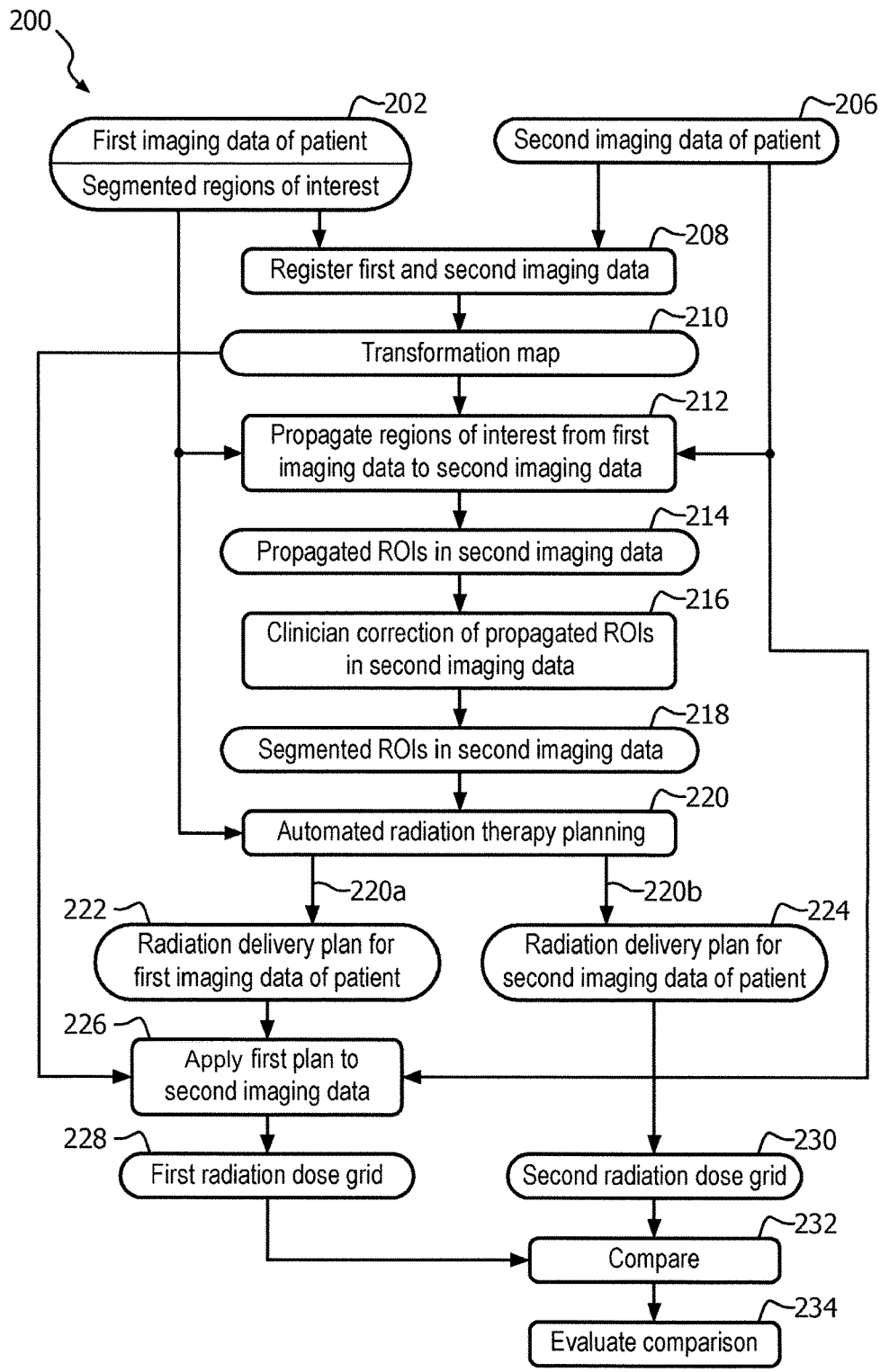

FIG. 1 schematically illustrates a typical radiation therapy delivery system 100; and FIG. 2 illustrates a method 200 for determining a utility of adaptive re-planning.

The present disclosure describes methods and systems for planning a radiation therapy treatment using a radiation therapy delivery system in conjunction with any one or more of various imaging system modalities. Such imaging system modalities include, for example, computed tomography (CT) imaging, cone beam CT, other x-ray based imaging, ultrasound imaging, magnetic resonance imaging (MRI), positron emission tomography (PET) imaging, and the like. A typical radiation therapy system 100 is schematically illustrated in FIG. 1. Thus, the system 100 includes a radiation source 102 for directing and providing radiation to designated target region(s) within a patient disposed on a support 104. The radiation source 102 may be, for example, an x-ray source, a linear accelerator, or some other suitable source for providing radiation for radiation therapy. The radiation source 102 source emits radiation as a beam having a single direction of travel and a cross-sectional area along that direction, somewhat like a laser sight emitter. The radiation source 102 is mounted on a movable support structure (not shown) so that it may be maneuvered to various positions and orientations around the patient for directing and providing radiation to the targeted regions within the patient. The targeted regions may include, for example, a cancerous tumor in the patient. In many cases, the radiation source 102 will have one or more accessories (not shown) such as a multi-leaf collimator or a wedge in order to customize and vary the radiation beam cross-sectional shape and intensity to be delivered from each position. In this way, the radiation therapy treatment planning and delivery process may be highly customized to meet the patient's needs.

The radiation therapy system 100 additionally includes a control console 106. The control console 106 has a radiation treatment delivery module 108 to move and operate the radiation source 102 through a wired or wireless communication link 110. The control console 106 includes one or more processors and a memory for performing those operations and other tasks. Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like. The Logic of the radiation treatment delivery module 108 may most easily be embodied as part of a software package.

The methods and systems described herein can be implemented on a variety of platforms including, for example, networked control systems and stand-alone control systems. Additionally, the logic shown and described herein preferably resides in or on a computer readable medium. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The control console 106 further includes a radiation therapy planning module 112 with one or more processors and a memory. The radiation therapy planning module 112 includes tools to create and/or import regions of interest, such as targeted regions and protected regions. The radiation therapy planning module 112 further includes tools to compute and/or import radiation dose grids, based on the regions of interest for example. A radiation dose grid identifies the radiation dosage which will be delivered to each voxel or pixel point within the patient's imaging space by a given radiation therapy plan. The module 112 is able to load multiple imaging data sets, and the regions of interest and radiation dose grids may be associated with multiple imaging data sets.

The control console 106 has a display 114 and an input device 116 such as a mouse and/or keyboard for user interaction with the radiation treatment delivery module 108 and the radiation treatment planning module 112.

The exemplary console 106 incorporates both a radiation treatment delivery module 108 and a radiation treatment planning module 112. In other embodiments, the two modules 108 and 112 may be incorporated in different consoles which are physically separated from each other. Thus, in such embodiments, the radiation planning module 112 is used to generate a radiation delivery plan. The generated plan may then be stored into memory and transferred to the radiation delivery module 108 for implementation at a later time.

FIG. 2 illustrates a method 200 for determining a utility of performing an adaptive re-planning. The method 200 may be implemented by a radiation therapy planning system, such as the module 112 discussed above or may be implemented in other forms of therapy planning, including, for example, proton therapy, ablation, or HIFU therapy. The illustrated exemplary method 200 contains several steps. Further embodiments of a suitable method for determining a utility of adaptive re-planning may include other additional steps, or omit one or more of the steps in the illustrated method 200. Also, the order in which the process flows herein have been described is not critical and can be rearranged while still accomplishing the same results. Thus the process flows described herein may be rearranged, consolidated, and/or re-organized in their implementation as warranted or desired.

The method 200 begins with a first imaging data set 202 of the patient. The first imaging data set 202 is a detailed two- or three-dimensional imaging scan of the patient's body or a pertinent portion thereof, such as a computed tomography (CT) scan. The first imaging data set 202 contains segmented regions of interest 204, including at least one or more targeted regions and perhaps one or more protected regions within the patient's body. The protected regions may include, for example, one or more organs at risk (OAR) of unhealthy exposure to radiation as a result of the therapy. The targeted and protected region segmentation 204 may be used by a clinician to prepare a radiation treatment delivery plan for the patient, based on the first imaging data set 202.

The method 200 also begins with a second imaging data set 206 of the patient. The second imaging data set 206 is a detailed two- or three-dimensional imaging scan of the patient's body or a pertinent portion thereof, such as a computed tomography (CT) scan. The second imaging data set 206 is recorded at a later time than the first imaging data set 202. In many typical applications of the method 200, a clinician will have used the first imaging data set 202 to generate a radiation therapy plan for the patient, and the second imaging data set 206 is produced closer in time to the planned radiation delivery to the patient. The respective portion(s) of the patient's body represented by the first imaging data 202 and the second imaging data 206 overlap at least to some extent. For example, they may both include the same targeted tumor region(s), and also include the same protected healthy region(s) immediately adjacent to the targeted tumor region(s).

Therefore, in step 208 of the method 200, the first imaging data set 202 and the second imaging data set 206 are registered with one another. The registration step 208 results in a transformation map 210, which represents the differences in position of a given imaging element (i.e. voxel or pixel) between the first imaging data 202 and the second imaging data 206. Various suitable imaging registration 208 techniques are currently known in the art, and are also the subject of ongoing research and development at the time of the present disclosure. The registration 208 may, for example, include rigid transformations as well as or in addition to non-rigid or deformable transformations. A representative registration 208 process is described in U.S. Provisional Patent Application Ser. No. 61/676,362, filed on Jul. 27, 2012, now U.S. Pat. No. 9,498,645, which is hereby incorporated by reference into this present specification for its registration-related description.

In step 212 of the method 200, the segmented regions of interest 204 in the first imaging data set 202 are propagated to the second imaging data set 206. That is, the transformation map 210 is applied to the borders defining the first segmented regions of interest 204, thereby mapping those borders to the second imaging data set 206. This propagation 212 of the first segmented regions of interest 204 results in one or more propagated regions of interest 214 in the second imaging data set 206, all as automatically calculated pursuant to the transformation map 210. In step 216 of the method 200, a clinician may in some embodiments be given the opportunity to manually correct or adjust the propagated regions of interest 214 to determine a final segmented set of regions of interest 218 in the second imaging data set 206. Other embodiments may omit the clinician correction step 216, instead using the propagated regions 214 as the final segmentation 218 without clinician involvement. Each segmented region of interest 218 in the second imaging data set 206 corresponds to one of the segmented regions of interest 204 in the first imaging data set 202, taking into account the change in position of the respective region(s) during the passage of time between the respective recordings of the first and second imaging data sets 202 and 206.

The next step 220 of the method 200 includes two separate and independent sub-steps 220a and 220b. In the first step 220a, an automated inverse radiation therapy planning technique 220 is applied to the first imaging data set 202. Thus a clinician specifies desired radiation delivery characteristics using the segmented regions of interest 204 of the first imaging data set 202. The technique 220 is "automated", which as defined herein means that the only user involvement in the planning process 220 is the entry of the desired radiation delivery characteristics by the clinician. These desired radiation characteristics can include for example a minimum radiation dosage to be delivered to each targeted region and a maximum radiation dosage to be delivered to each protected region. The desired radiation characteristics are entered into a radiation therapy planning system, such as the module 112 described above. The planning system applies any one or more of several algorithms known in the art presently or hereafter to generate a first radiation delivery plan 222. The first radiation delivery plan 222 corresponds to a set of parameters which may be used by a radiation delivery system, such as the system 100 described above, to deliver the desired radiation characteristics entered by the clinician within some margin of error. Such system parameters may include, for example, a series of radiation beam orientations, radiation beam field shapes or aperture settings, and radiation beam energies. A representative planning process 220 is described in U.S. Provisional Patent Application Ser. No. 61/719,528, filed on Oct. 29, 2012, now U.S. Pat. No. 9,943,702, which is hereby incorporated by reference into this present specification for its planning-related description.

In some cases, the automated inverse radiation therapy planning technique 220 will have already been applied to the first imaging data set 202 to generate a first radiation delivery plan 222. This may have happened, for example, as part of an earlier radiation therapy planning process based on the data 202. If such an automatically generated 220 plan 222 does indeed already exist, the step 220a may be accomplished by simply loading the plan 222 into the memory of the radiation therapy planning system.

In step 220b of the method 200, the automated inverse radiation therapy planning technique 220 is applied to the second imaging data set 206. This step 220b uses the same technique 220 which is used in step 220a. That is, a clinician specifies desired radiation delivery characteristics using the segmented regions of interest 218 of the second imaging data set 206. Then a radiation therapy planning system generates a second radiation delivery plan 224. The second plan 224 is a set of radiation delivery system parameters which may be used to deliver the desired radiation characteristics entered by the clinician within some margin of error.

As indicated above, the only user involvement in the planning process 220 is the entry of the desired radiation delivery characteristics by the clinician. This automation greatly increases the speed with which the process 220 may be implemented to generate the radiation delivery plans 222 and 224. But, it also means the resulting plans 222 and 224 are not clinically certified, so they should not be actually delivered to a patient. Rather, their use within the method 200 is simply a fast and efficient means to determine the utility of a clinician actually performing a re-planning of the patient due to changed circumstances which arose between the time of the first imaging data 202 and the time of the second imaging data 206. Thus, the automated plans 222 and 224 may be labeled with appropriate electronic tags to indicate they should not be used to actually deliver radiation to a real patient, unless and until they are clinically approved by an appropriate medical professional.

In step 226 of the method 200, the radiation therapy planning system applies the first radiation delivery plan 222 to the second imaging data set 206. That is, the planning system determines the radiation dose grid resulting to the second imaging data set 206 if the first radiation delivery plan 222 were applied to the patient as represented by the second imaging data set 206. The transformation map 210 can be used for this purpose. This results in a first radiation dose grid 228. The first radiation dose grid 228 identifies the radiation dosage received at each imaging element voxel or pixel in the second imaging data set 206 of the patient by the first radiation delivery plan 222.

The radiation therapy planning system further generates a second radiation dose grid 230 based on the second radiation delivery plan 224 being applied to the second imaging data set 206. The second radiation dose grid 230 identifies the radiation dosage received at each imaging element voxel or pixel in the second imaging data set 206 of the patient by the second radiation delivery plan 224.

In step 232 of the method 200, the first radiation delivery plan 222 and the second radiation delivery plan 224 are compared. That is, the radiation therapy planning system compares each one of the grids 228 and 230 to the desired radiation delivery characteristics specified by the clinician in step 220b. The comparison 232 may take many forms, which can be either qualitative or quantitative, as known in the art presently or hereafter. For example, the radiation therapy planning system may generate a first map identifying the differences between the first radiation dose grid 228 and the desired radiation delivery characteristics, for each imaging element (i.e. voxel or pixel) of the second imaging data 206. A similar map can be generated for the second radiation dose grid 230, and qualitatively compared to the first map by a clinician's visual inspection. The comparison 232 may alternatively or additionally be a quantitative calculation. Thus, the imaging element differences may be summed up, averaged, or otherwise mathematically analyzed to quantify the respective differences between the radiation dose grids 228 and 230 and the desired radiation delivery characteristics specified by the clinician in step 220b.

In the final step 234 of the method 200, the results of the comparison 232 are evaluated to determine a utility of re-planning the patient. If the second radiation delivery plan 224 is determined to produce materially better results than the first radiation delivery plan 222, then the method 200 suggests there is utility in clinically re-planning the patient before delivering radiation therapy. If not, then the method 200 suggests the benefits which might be obtained from clinically re-planning the patient are not worth the required time and effort, so there is no utility in re-planning. Whether one of the radiation dose grids 228 and 230 is "materially" better than the other will depend heavily on the particular clinical context and goals of the radiation therapy being contemplated for each individual patient. The purpose of the method 200 is to provide a framework for an automatic estimation of quality improvements which is independent of clinician bias.

The invention has been described with reference to the several embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various compositions, components and arrangements, combinations and sub-combinations of the elements of the disclosed embodiments.

Having thus described several embodiments, the invention is now claimed to be:

1. A therapy planning method for determining a utility of performing a re-planning on a patient, the method comprising:
   registering a first imaging data set of the patient with a second imaging data set of the patient to generate a transformation map, wherein the first imaging data set comprises at least one segmented region of interest, and the second imaging data set is recorded at a later time than the first imaging data set;
   propagating the at least one segmented region of interest in the first imaging data set to the second imaging data set utilizing the transformation map, to generate a corresponding segmented region of interest in the second imaging data set;
   applying an automated inverse therapy planning technique to the first imaging data set based on one or more user-specified desired delivery characteristics derived from the first imaging data set, to generate a first delivery plan;
   applying the automated inverse therapy planning technique to the second imaging data set based on the one or more user-specified desired delivery characteristics derived from the second imaging data set, to generate a second delivery plan;
   applying the first delivery plan to the second imaging data set, to generate a first dose grid identifying a dosage received at each voxel or pixel of the second imaging data set by the first delivery plan;
   generating a second dose grid identifying a dosage received at each voxel or pixel of the second imaging data set by the second delivery plan; and
   comparing the first dose grid and the second dose grid to generate a plan comparison and determining the utility of performing the re-planning based on the comparison.

2. The method of claim 1, wherein the first imaging data set comprises at least one segmented targeted region of interest and at least one segmented protected region of interest, and the propagation step includes propagating the targeted region of interest and the protected region of interest, and the user-specified desired delivery characteristics comprise a minimum dosage to be applied to the targeted region and a maximum dosage to be applied to the protected region.

3. The method of claim 1, wherein the desired characteristics comprise a minimum dosage to be delivered to a segmented targeted region of interest in the second imaging data set.

4. The method of claim 1, wherein before the method is applied a clinician has already used the first imaging data set to generate an initial therapy plan for the patient, and the second imaging data set is produced closer in time to a delivery the initial plan to the patient.

5. The method of claim 1, wherein the first delivery plan exists prior to implementation of the method, and the step of applying the automated inverse therapy planning technique to the first imaging data set corresponds to loading the pre-existing first delivery plan into a memory of a therapy planning system.

6. The method of claim 1, wherein the therapy is one of radiation therapy, particle therapy, ablation therapy or HIFU therapy.

7. The method of claim 1, further comprising the step of providing a user with an opportunity to manually adjust a propagated region of interest in order to generate the corresponding segmented region of interest.

8. The method of claim 1, further comprising the step of applying electronic tags to the first and second delivery plans to indicate the plans have not been clinically approved for actual delivery to the patient.

9. The method of claim 1, further comprising the step of evaluating the plan comparison to determine the utility of re-planning the patient.

10. The method of claim 1, wherein the comparing step further comprises:
comparing each one of the first and second dose grids to the one or more user-specified desired delivery characteristics derived from the second imaging data set.

11. The method of claim 10, wherein the comparing step further comprises:
generating a first map identifying differences between the first dose grid and the user-specified desired delivery characteristics derived from the second imaging data set, and a second map identifying the differences between the second dose grid and the user-specified desired delivery characteristics derived from the second imaging data set.

12. The method of claim 10, wherein the comparing step further comprises:
a numerical analysis of respective differences between the first and second dose grids and the user-specified desired delivery characteristics derived from the second imaging data set.

13. A non-transitory computer-readable medium carrying software configured to control a computer processor to perform the method of claim 1.

14. The therapy planning method of claim 1, wherein the first and second delivery plans are generated independently of clinician input beyond the user-specified delivery characteristics and are not approved for use on the patient.

15. The therapy planning method of claim 1, further including:
labeling the automatically generated first and second treatment plans with electronic tags indicating they should not be used to deliver radiation to a patient.

16. A system for determining a utility of performing a re-planning on a patient during a therapy planning, the system including:
a computer processor configured to:
register a first imaging data set of the patient with a second imaging data set of the patient to generate a transformation map, wherein the first imaging data set comprises at least one segmented region of interest, and the second imaging data set is recorded at a later time than the first imaging data set;
propagate the at least one segmented region of interest in the first imaging data set to the second imaging data set utilizing the transformation map, to generate a corresponding segmented region of interest in the second imaging data set;
apply an automated inverse therapy planning technique to the first imaging data set based on one or more user-specified desired delivery characteristics derived from the first imaging data set, to generate a first delivery plan;
apply the automated inverse therapy planning technique to the second imaging data set based on one or more user-specified desired delivery characteristics derived from the second imaging data set, to generate a second delivery plan;
apply the first delivery plan to the second imaging data set, to generate a first dose grid identifying a dosage received at each voxel or pixel of the second imaging data set by the first delivery plan;
generate a second dose grid identifying a dosage received at each voxel or pixel of the second imaging data set by the second delivery plan; and
compare the first dose grid and the second dose grid to generate a plan comparison and determine the utility of performing the re-planning based on the comparison of the first and second delivery plans.

17. The system of claim 16, wherein the computer processor is configured to provide a user with an opportunity to manually adjust a propagated region of interest in order to generate the corresponding segmented region of interest.

18. The system of claim 16, further including:
a display device configured to display at least one of the first image data set, the second image data set, the first dose grid, the second dose grid, and the plan comparison.

19. The system of claim 16, wherein the computer processor is further configured to evaluate the plan comparison to determine a utility of re-planning the patient.

20. The system of claim 16, wherein the computer processor is further configured to compare each one of the first and second dose grids to the user-specified desired delivery characteristics derived from the second imaging data set.

* * * * *